(12) United States Patent
Ailinger et al.

(10) Patent No.: US 6,530,881 B1
(45) Date of Patent: Mar. 11, 2003

(54) SHEATH APPARATUS FOR ENDOSCOPES AND METHODS FOR FORMING SAME

(75) Inventors: Robert E. Ailinger, Norwood, MA (US); Stephen M. Martone, Westford, MA (US); Katsumi Oneda, Alpine, NJ (US); Mark S. Landman, Sharon, MA (US)

(73) Assignee: Vision Sciences, Inc., Natick, MA (US)

( * ) Notice: Subject to any disclaimer, the term of this patent is extended or adjusted under 35 U.S.C. 154(b) by 104 days.

(21) Appl. No.: 09/611,628

(22) Filed: Jul. 7, 2000

Related U.S. Application Data

(63) Continuation-in-part of application No. 09/235,355, filed on Jan. 21, 1999, now Pat. No. 6,350,231.

(51) Int. Cl.7 .................................................. A61B 1/04
(52) U.S. Cl. ...................................... 600/121; 600/114
(58) Field of Search ................................ 600/121, 114; 604/347

(56) References Cited

U.S. PATENT DOCUMENTS

| | | | |
|---|---|---|---|
| 3,794,091 A | 2/1974 | Ersek et al. ............... 150/52 R |
| 3,805,770 A * | 4/1974 | Okada ......................... 600/114 |
| 3,809,072 A | 5/1974 | Ersek et al. .................. 128/23 |
| 4,143,423 A * | 3/1979 | Sternlieb .................... 128/844 |
| 4,794,920 A * | 1/1989 | Robichaud .................. 604/349 |
| 4,881,553 A * | 11/1989 | Grossman .................. 128/844 |
| 4,886,049 A | 12/1989 | Darras .......................... 128/4 |
| 4,971,071 A * | 11/1990 | Johnson ..................... 128/842 |
| 5,098,755 A * | 3/1992 | Tanquary et al. ........... 428/156 |
| 5,111,831 A * | 5/1992 | Foggia ....................... 128/842 |
| 5,237,984 A | 8/1993 | Williams, III et al. ......... 128/4 |
| 5,337,734 A * | 8/1994 | Saab ........................... 600/121 |
| 5,419,310 A | 5/1995 | Frassica et al. ................ 128/4 |
| 5,429,118 A * | 7/1995 | Cole et al. .................. 600/121 |
| 5,443,781 A | 8/1995 | Saab .......................... 264/291 |
| 5,482,053 A * | 1/1996 | Kelly .......................... 128/844 |
| 5,483,951 A | 1/1996 | Frassica et al. ............ 600/104 |
| 5,505,686 A | 4/1996 | Willis et al. ................ 600/104 |
| 5,513,654 A * | 5/1996 | Delson ........................ 128/844 |
| 5,570,692 A * | 11/1996 | Morinaga ................... 600/453 |
| 5,643,175 A | 7/1997 | Adair .......................... 600/133 |
| 5,695,454 A | 12/1997 | Mourkidou ................. 600/166 |
| 5,718,861 A | 2/1998 | Andrews et al. ............ 264/235 |
| 5,881,386 A * | 3/1999 | Horwege et al. ............ 2/161.7 |
| 6,270,484 B1 * | 8/2001 | Yoon .......................... 604/264 |
| 6,293,907 B1 * | 9/2001 | Axon et al. ................. 600/114 |

* cited by examiner

Primary Examiner—Linda C. M. Dvorak
Assistant Examiner—Jocelyn Ram
(74) Attorney, Agent, or Firm—Dorsey & Whitney LLP

(57) ABSTRACT

A thin-walled elastic sheath that can be stretched axially over an elongated imaging device to closely conform to the device and isolate the device from an external environment, and a method of forming such a sheath, are shown and described. The method includes the steps of heating at least a portion of a sheet of an elastomeric material to an elevated temperature to form a malleable heated portion of the sheet, pressing an elongated forming tool against the sheet at a location central with respect to the heated portion of the sheet, stretching the heated portion of the elastomeric material with the forming tool until an elastic conforming portion of the sheet is conformed to at least a portion of the length of the forming tool, and removing the forming tool from the conforming portion of the sheet to leave the thin-walled, elastic sheath having a wall thickness approximately equal to or less than 0.006 inches.

90 Claims, 12 Drawing Sheets

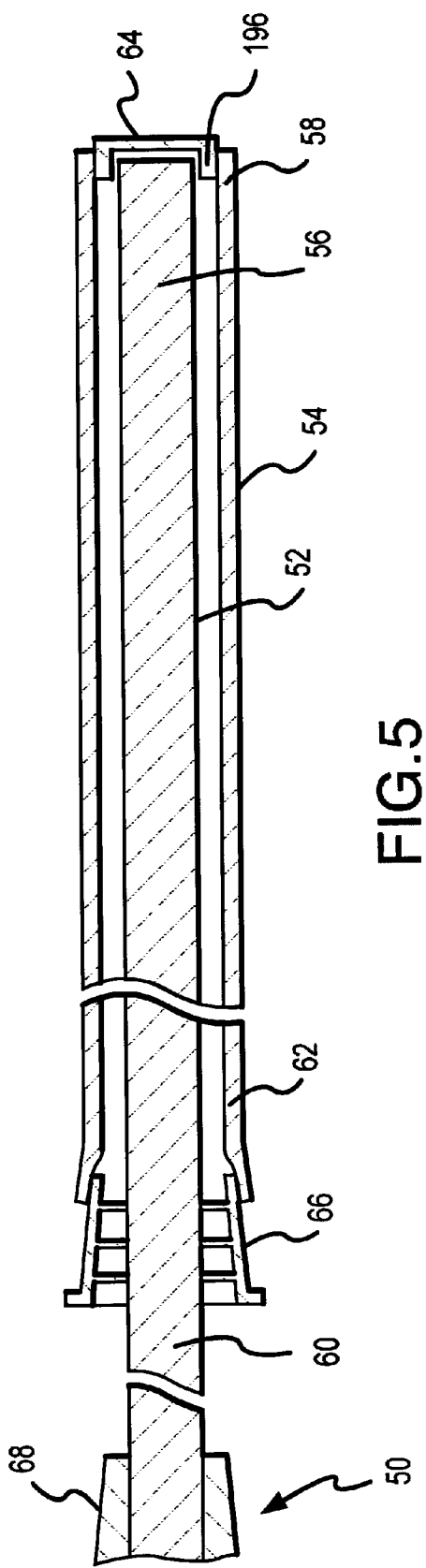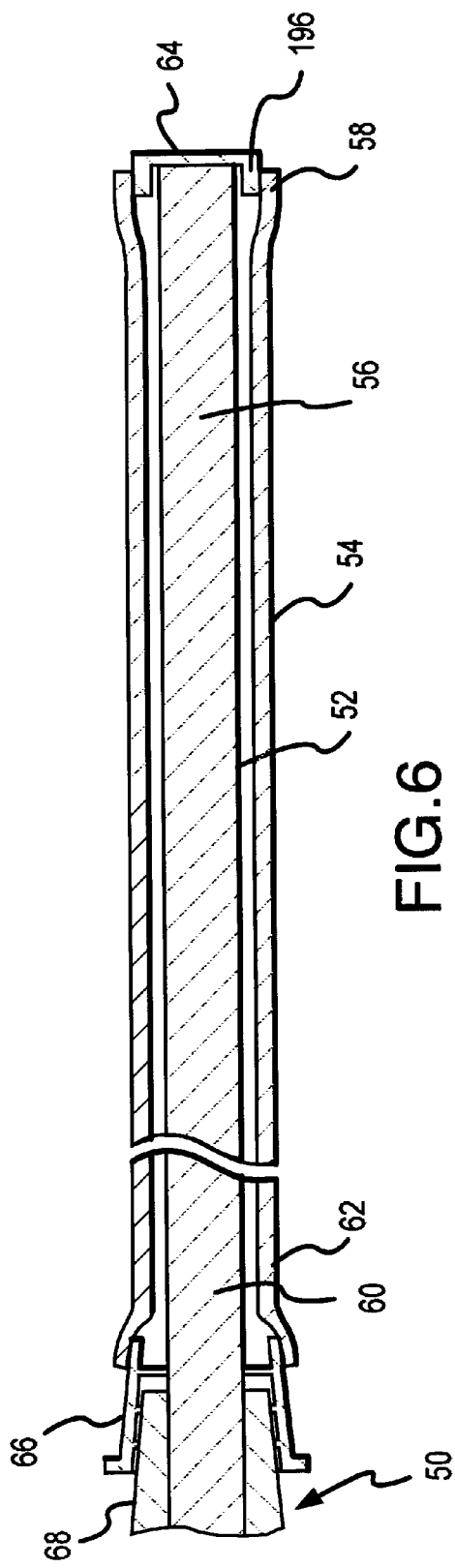

SHEATH APPARATUS FOR ENDOSCOPES AND METHODS FOR FORMING SAME

CROSS-REFERENCE TO RELATED APPLICATIONS

This application is a continuation-in-part of U.S. patent application No. 09/235,355, filed Jan. 21, 1999 now U.S. Pat. No. 6,350,231.

TECHNICAL FIELD

The present invention is directed toward elongated imaging components and a method of making the components, and, more particularly, toward thin-walled, elastic sheaths for elongated imaging equipment and a method of making the same.

BACKGROUND OF THE INVENTION

The use of intrabody medical equipment, such as endoscopes, catheters, and the like, for diagnostic and therapeutic indications is rapidly expanding. To improve performance, the equipment has been optimized to best accomplish the selected purpose. As an example, endoscopes have been optimized and refined so as to provide upper endoscopes for the examination of the esophagus, stomach, and duodenum, colonoscopes for examining the colon, angioscopes for examining blood vessels, bronchoscopes for examining bronchi, laparoscopes for examining the peritoneal cavity, arthroscopes for examining joints and joint spaces, nasopharygoscopes for examining the nasal passage and pharynx, and intubation scopes for examination of a person's airway.

Optimization of intrabody medical equipment for such therapeutic and diagnostic procedures has resulted in sterile, inexpensive disposable components that are used alone or with non-disposable equipment. In the field of endoscopes, a conventional endoscope 10, shown in FIG. 1, has an insertion tube 12 connected at its proximal end 14 to a handle or control body 16. The insertion tube 12 is adapted to be inserted into a patient's body cavity to perform a selected therapeutic or diagnostic procedure. The insertion tube 12 contains an imaging system 18 having optical fibers or the like extending along the length of the insertion tube and terminating at a viewing window 19 in the insertion tube's distal end 20. The imaging system 18 conveys an image from the viewing window 19 to an eyepiece 22 on the control body 16 or to a monitor (not shown), so the user can see into a selected body cavity during an endoscopic procedure. The endoscope 10 is described in greater detail in U.S. Pat. No. Re 34,110 and U.S. Pat. No. 4,646,722, which are incorporated herein by reference.

Disposable endoscopic sheath assemblies are used to cover the insertion tube 12 and protect it from contaminating a patient during use. Accordingly, the sheath assemblies alleviate the problem and cost of cleaning and sterilizing the insertion tube 12 between endoscopic procedures. The sheaths and endoscopes are usable in medical applications and also in industrial applications, such as visually inspecting difficult to reach areas in an environment that could damage or contaminate the endoscope. As an example, a sheathed endoscope can be used in an industrial area wherein the sheath protects the endoscope's insertion tube from adhesive or the like. As seen in FIG. 1, a conventional sheath assembly 24, shown partially cut away for illustrative purposes, includes a sheath 26 that surrounds the endoscope's insertion tube 12. The sheath assembly 24 may also contain one or more working channels 32 that extend along the insertion tube 12 and that are adapted to receive conventional endoscopic accessories therethrough without allowing the endoscope to contaminate the accessories during the endoscopic procedure. The sheath 26 has a distal end portion 21 that includes an endcap 34 having a transparent window 28 positioned to cover the viewing window 19 at the insertion tube's distal end 20 when the sheath assembly 24 is installed. The endcap 34 is sealably secured to the sheath's distal end portion 21.

The sheath 26 and endcap 34 are commonly made from polymeric materials. The sheath 26 can be made from an inelastic polymer, such as PVC, acrylic, polycarbonate, polyethylene terephthalate or other thermoplastic polyesters, or can be made from an elastomeric material. Both materials presently have advantages and disadvantages.

Inelastic materials allow for thin-walled medical components that exhibit high strength and visible clarity. Using inelastic materials, the sheath 26 can be formed with a thin wall (measuring 0.003 inches or less) and a small diameter (such as 0.5 mm). Inelastic materials tend to be clearer than the elastic materials, and can thus provide better visibility with less distortion.

U.S. Pat. No. 5,443,781 to Saab teaches a method of forming an inelastic, disposable sheath with an integral, optically transparent window. Saab teaches forming the inelastic sheath by heating a sheet or film of optically transparent, inelastic, polymeric material until the material is malleable. As shown in FIG. 2, a mandrel 35 is thrust into the heated film 37 causing the film to stretch and to generally conform to the mandrel's shape. As a result, the heated film 37 is formed into an inelastic closed-end sheath 39 having sidewalls 36, a flange or collar 38 at its open proximal end 40, and a closed distal end 42.

U.S. patent application Ser. No. 08/948,615, which is incorporated herein by reference, further teaches a method of forming an inelastic, endoscopic sheath for use on an insertion tube having a complex cross-sectional shape. The process applies a differential pressure to the outside and inside of the sheath during fabrication to conform the sheath to the shape of a mandrel. By selecting a mandrel with the proper complex shape, the end cap can closely receive the corresponding insertion tube.

Inelastic materials, however, have a number of disadvantages. Tight-fitting sheaths formed from inelastic materials may overly restrict bending when used with flexible insertion tubes. The insertion tube combined with the tight-fitting, inelastic sheath can only bend over a limited radius. If bent further, the sheath will either buckle, in the case of a thick-walled sheath, or the sheath material will become taught, in the cause of a thin-walled sheath, preventing the insertion tube from bending further. Consequently, if the inelastic sheath is to be used in combination with a flexible endoscope, the sheath is typically either baggy or must contain bending features, such as accordion-like baffles or the like, as taught by Saab, to allow the insertion tube to sufficiently bend. Both baggy sheaths and these additional bending features add to the cross-sectional size of the sheath during use, which may result in additional pain or discomfort to the patient.

The sheath made form inelastic material cannot be stretched axially onto the insertion tube. As a result, the inelastic sheath does not provide axial tension in the sheath urging the transparent window of the sheath against and in alignment with the viewing window at the insertion tube's distal end. To retain the transparent window in position, additional features, such as connectors or helical coils, are typically built into the sheath. These features add to the complexity and cost of the sheath.

Conventional elastic sheaths have been developed and used with imaging devices such as endoscopes to overcome the drawbacks associated with the inelastic sheaths described above and to provide additional benefits. As an example, conventional elastic sheaths are designed so the sheath will easily bend with the insertion tube without substantially affecting the insertion tube's bending characteristics. The elastic sheath can also be stretched axially over the insertion tube to provide axial tension that retains the transparent window on the sheath against and in alignment with the viewing window at the insertion tube's distal end. The elastic sheath can be designed to closely or tightly cover the insertions tube while still being able to bend with the insertion tube, so the elastic sheath does not need additional bending features.

Elastic materials, however, also have some disadvantages. First, conventional elastic sheaths are manufactured by extruding elastomeric material. The extruded elastic sheaths, however, have manufacturing limits that restrict the minimum wall thickness of the sheath, particularly for sheaths having small internal diameter. Efforts toward manufacturing such a sheath have typically resulted in the extruded material collapsing or wrinkling and adhering to itself during the process. As a result, the extruded elastic sheath must be made with a relative thick wall (i.e., greater than 0.006 inches). The thicker the sheath wall in a tight-fitting sheath, the greater the resistance to bending.

Tight fitting, elastic sheaths can also be complex and expensive to install onto the insertion tube. The elastic materials commonly used to manufacture the sheath have high friction characteristics. As a result, it can be difficult to insert the insertion tube into the tight-fitting sheath because the insertion tube binds on the inner wall of the sheath. One solution is to make the sheath with a diameter considerably larger than the insertion tube, so the sheath is baggy when installed on the insertion tube. Baggy sheaths, however, are undesirable in many endoscopic procedures because the sheath can be twisted, bunched, or misaligned relative to the insertion tube during the procedure. The baggy sheath can also increase the diameter of the sheathed insertion tube, which can increase pain or discomfort to the patient. In another solution, a tight-fitting sheath and endoscope are specially designed to mate with a vacuum or inflation chamber (not shown) that radially expands the sheath while the insertion tube is inserted into the sheath. Once the insertion tube is fully inserted into the sheath, the vacuum or inflation pressure is removed and the sheath contracts to a size that fits closely over the insertion tube. The equipment needed for this installation process, however, as well as the time required to learn and perform the process, can significantly increase the cost of endoscopic procedures.

In the design of intrabody medical devices and accessories, including optical and non-optical devices, there is a need for components having the benefits of both elastic and inelastic materials while, at the same time, avoiding the disadvantages associated with these materials. As an example, there is a need for an elastic component that can be manufactured with both a thin wall and a small internal diameter. There is also a need for a small diameter, elastic sheath that can be quickly and inexpensively installed and used on a flexible insertion tube. Other medical devices and accessories would also benefit by such inexpensive, elastic, thin-walled components.

SUMMARY OF THE INVENTION

The present invention provides a method capable of forming thin-walled, elastic medical components from a heated, elastomeric sheet. The method of one particular embodiment of the invention may be used to manufacture small-diameter, thin-walled, elastic components, which has been problematic in the prior art. In an exemplary embodiment of the present invention, the method of forming a small-diameter, thin-walled elastic component includes heating a portion of the elastomeric sheet to a malleable temperature, pressing a distal end of an elongated forming tool on a first side of the elastomeric sheet at a location in the heated portion, stretching the heated portion with the forming tool until an elastic conforming portion is closely conformed to a portion of the forming tool, and removing the forming tool from the conforming portion of the sheet. The method of this embodiment can be used to form an elastic sheath having a thin wall, a small diameter, and a length shorter than the length of the insertion tube so that the elastic sheath may be stretched longitudinally over the insertion tube.

Embodiments of the present invention also provide a non-extruded thin-walled, elastic medical component made by the above-described process.

BRIEF DESCRIPTION OF THE DRAWINGS

FIG. 5 is a partial cross-sectional view of the sheath and endoscope of FIG. 3 as viewed along Section 5—5.

FIG. 6 is a partial cross-sectional view of the sheath and endoscope of FIG. 4 as viewed along Section 6—6.

DETAILED DESCRIPTION OF THE INVENTION

The present detailed description is generally directed toward elastomeric sheaths for medical devices, and toward a method for forming such sheaths from a sheet of an elastomeric material. Many specific details of certain embodiments of the invention are set forth in the following description and in FIGS. 3–10 to provide a thorough understanding of such embodiments. One skilled in the art, however, will understand that the present invention may have additional embodiments, or that the invention may be practiced without several of the details described in the following description.

Figure 1:
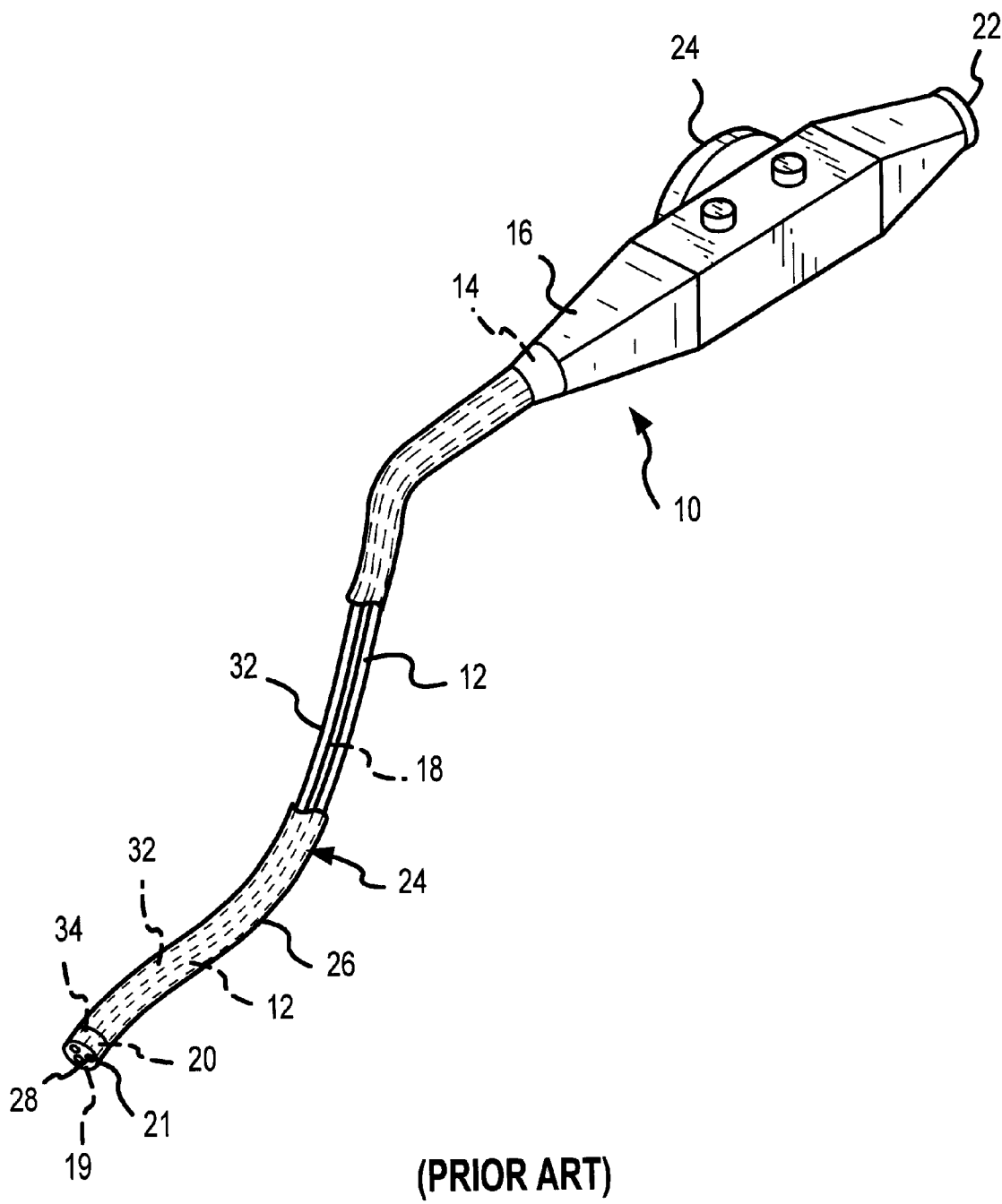
FIG. 1 is an isometric view of a prior art endoscope and endoscopic sheath assembly.
Figure 2:
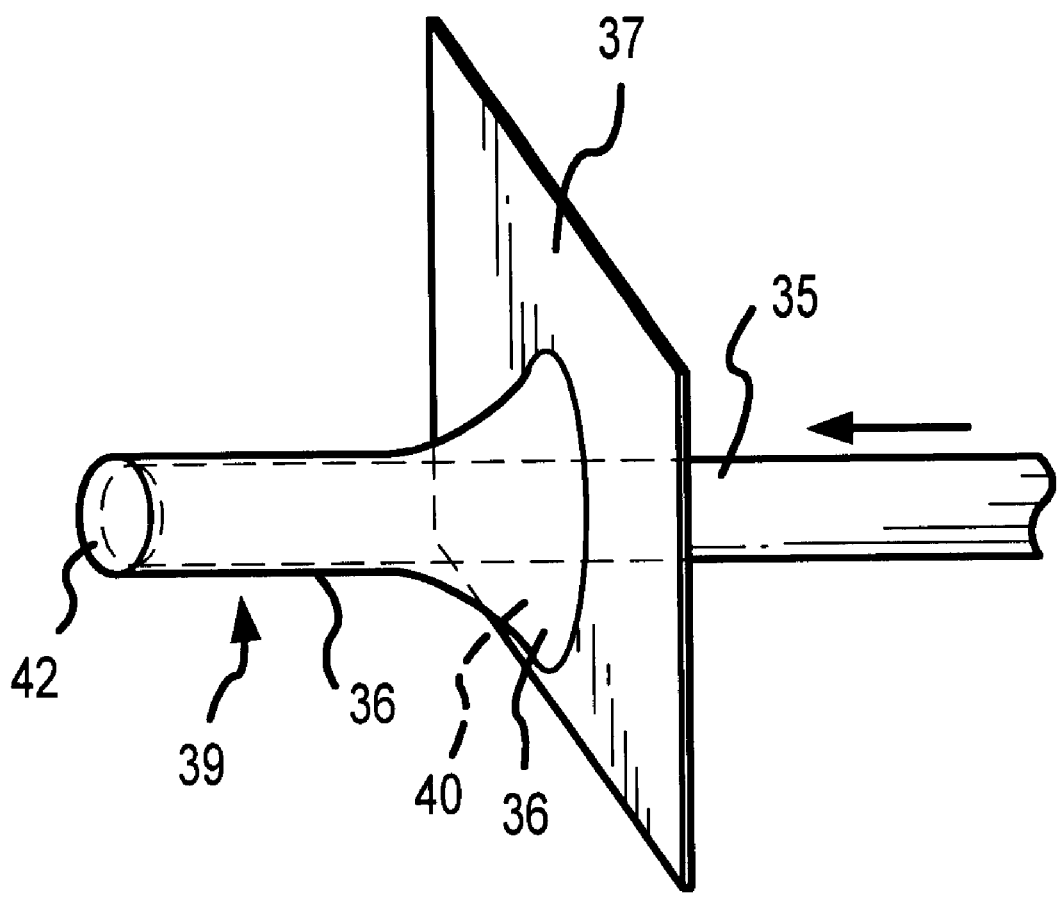
FIG. 2 is an isometric view of an inelastic film of the prior art being stretched by a mandrel.
Figure 3:
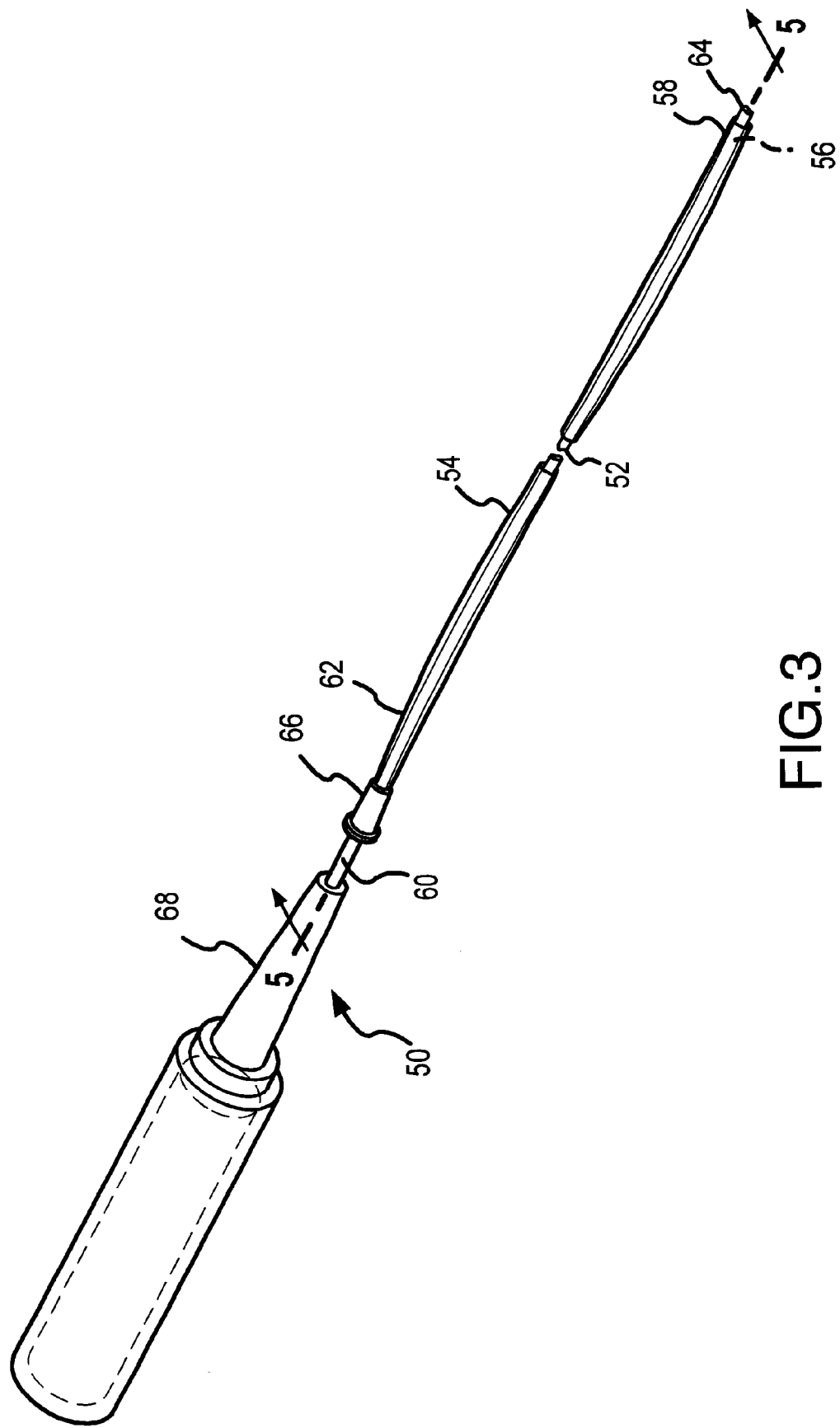
FIG. 3 is an isometric view of a thin-walled, elastic sheath formed in accordance with one embodiment of the present invention placed in a relaxed state over an insertion tube of a flexible endoscope.

FIGS. 3–6 illustrate a medical device, for example an endoscope 50 having an insertion tube 52, and a non-extruded, thin-walled, elastic sheath 54 formed in accordance with an embodiment of the invention. As best seen in FIGS. 3 and 5, the elastic sheath 54 is shaped and sized so its diameter is slightly larger than the insertion tube's diameter. The insertion tube 52 can be easily inserted into the elastic sheath 54 until a distal end 56 of the insertion tube 52 just contacts a distal end 58 of the elastic sheath 54. The elastic sheath 54 in FIG. 3 is thus in its relaxed state, having a relaxed outside diameter, a relaxed inner diameter, and a relaxed wall thickness. The elastic sheath 54 has a relaxed wall thickness in the range of up to and including approximately 0.009 inches, and preferably in the range of approximately 0.002 to 0.009 inches, inclusive, and more preferably in the range of approximately 0.002 to 0.006 inches, inclusive.

Figure 4:
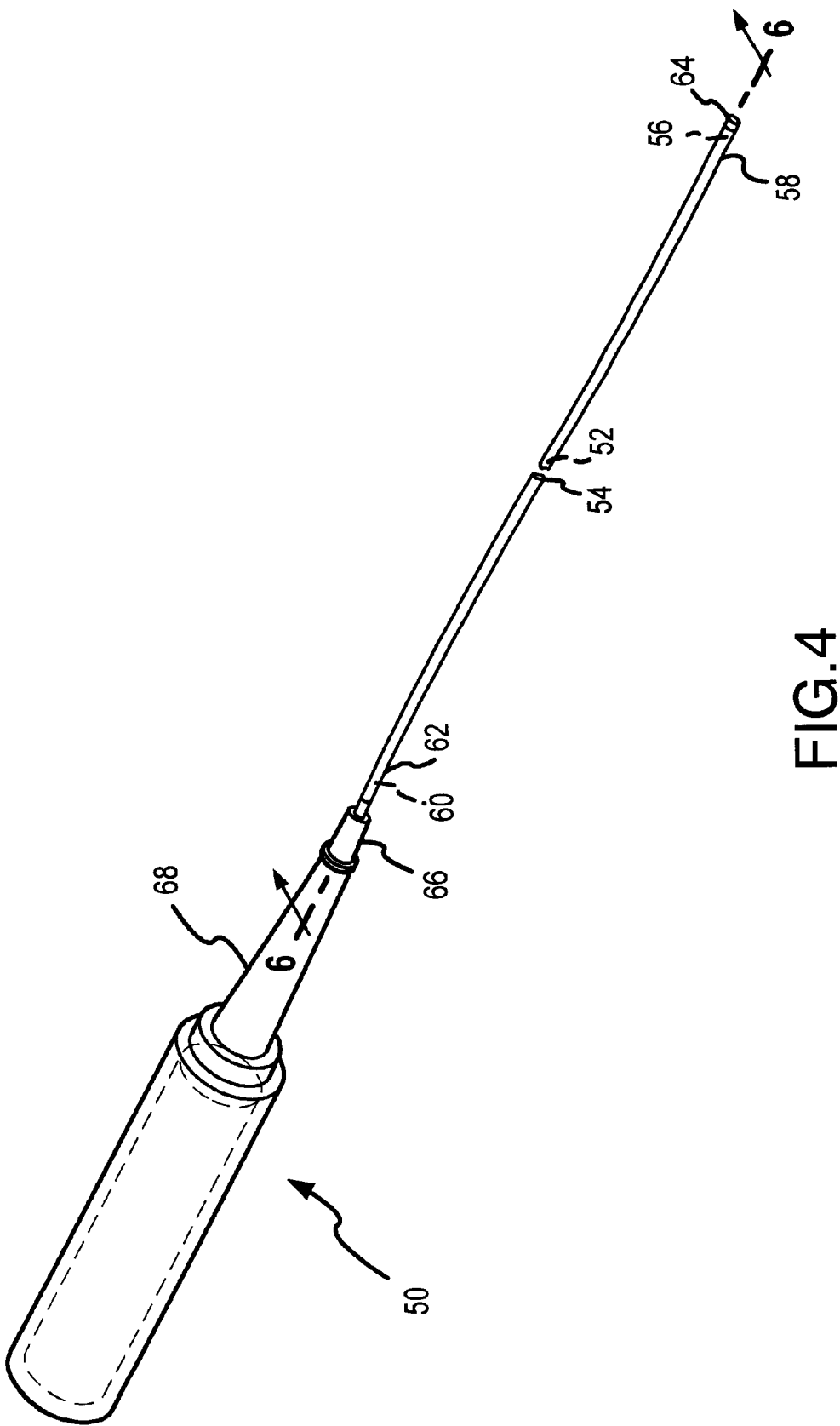
FIG. 4 is an isometric view of the sheath of FIG. 3 in an installed position stretched axially over the insertion tube of the flexible endoscope.

FIGS. 4 and 6 illustrate the elastic sheath 54 stretched axially over the insertion tube 52 until a proximal end 62 of the elastic sheath 54 aligns with a proximal end 60 of the insertion tube 52. The elastic sheath 54 is thus in a stretched, installed position, having a stretched outside diameter, a stretched inner diameter, and stretched wall thickness. The stretched inner diameter, stretched outer diameter, and a stretched wall thickness illustrated in FIG. 6 are smaller than the similar dimensions relaxed in FIG. 5. When the elastic sheath 54 is in the installed position over the insertion tube 52, the elastic sheath and endoscope are ready for use in an endoscopic procedure while the insertion tube remains isolated from a contaminated environment.

As best seen in FIGS. 5 and 6, the extreme distal end 58 of the elastic sheath 54 is sealably connected to an end cap 64. The end cap 64 can be integral with the elastic sheath 54, or can be formed separately from the sheath and sealably attached thereto. In the latter case, the end cap 64 can be formed from a different material than the elastic sheath 54, such as an inelastic polymer, in order to provide selected optical characteristics that may be different than those of the elastomeric material. For example, the end cap 64 can be formed from a clear, inelastic polymer to provide better visibility for use with an insertion tube 52 having a viewing window at its distal end 56.

The proximal end 62 of the elastic sheath 54 terminates in a fitting, such as a collar 66. Similar to the end cap 64, the collar 66 can be integral with the sheath 54 or separate from and bonded to the elastic sheath 54. As best illustrated in FIG. 6, the collar 66 is sized and shaped to resiliently engage a headpiece 68 of the endoscope 50 to retain the sheath 54 on the insertion tube 52 during a procedure.

Figure 7:
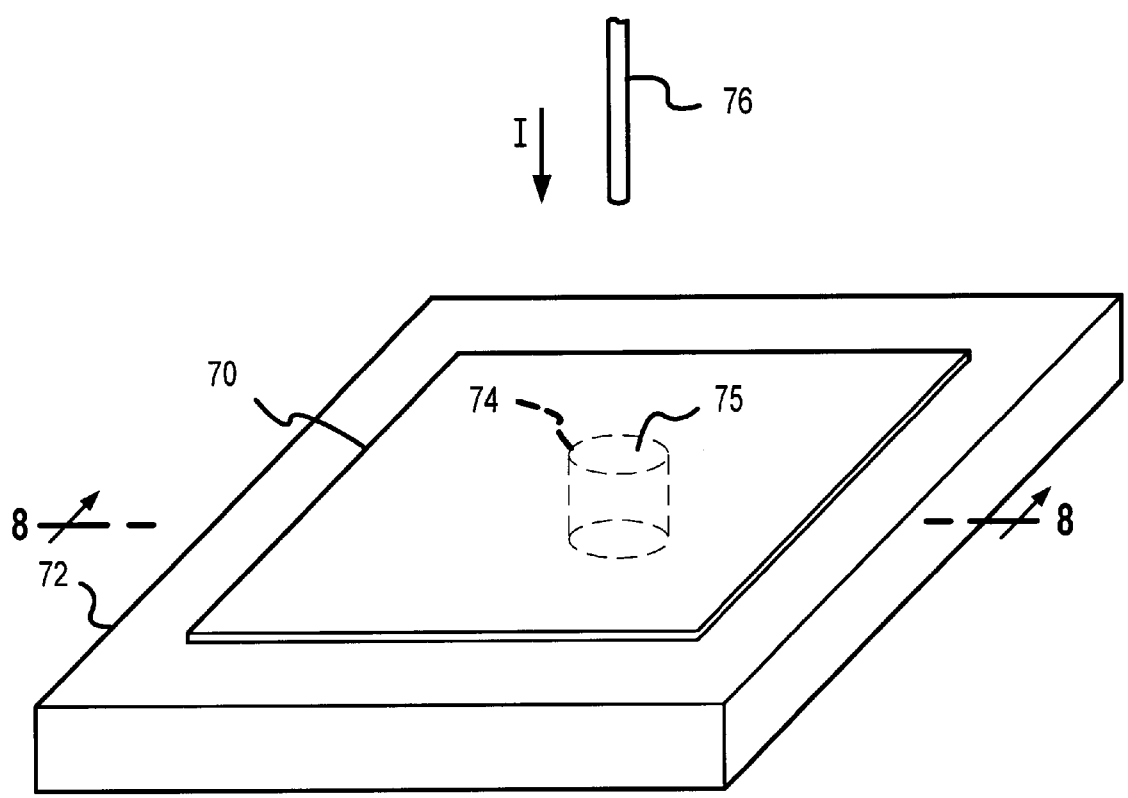
FIG. 7 is an isometric view of a sheet of partially-heated, elastomeric material and a support structure below a forming tool according an embodiment of the method of the present invention before the sheath has been formed.
Figure 8:
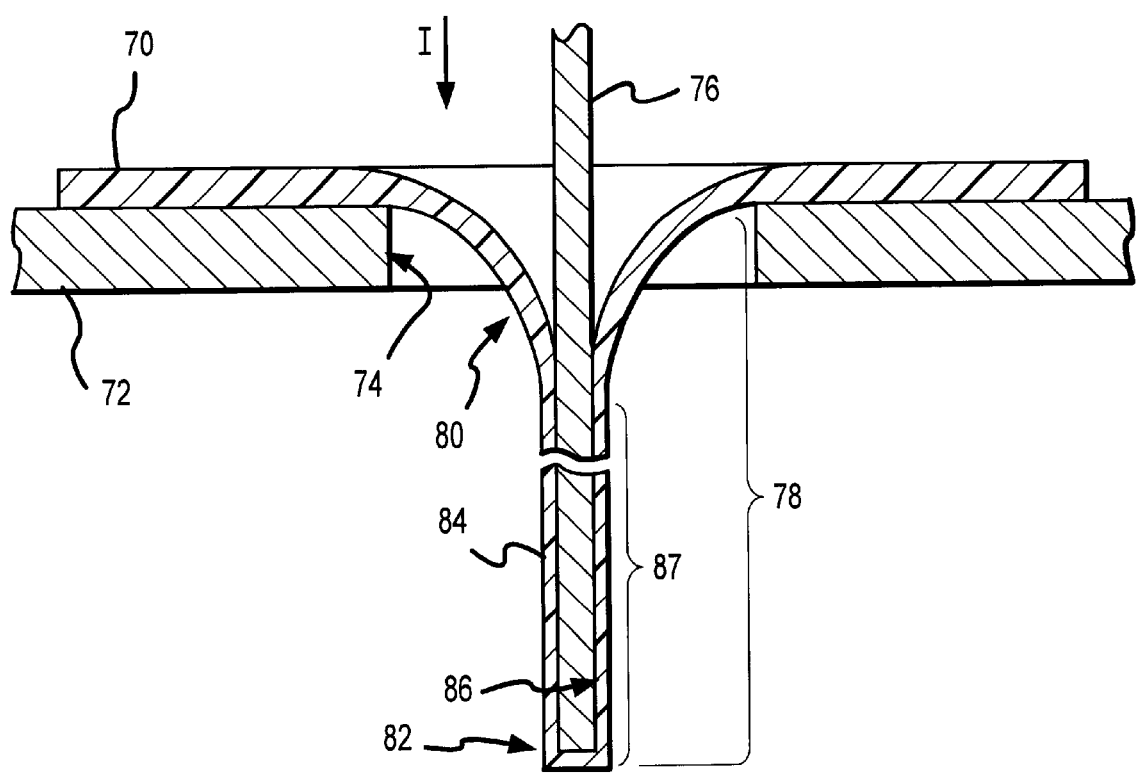
FIG. 8 is an enlarged cross-sectional view of FIG. 7 viewed along Section 8—8 after the sheath has been formed.

FIGS. 7 and 8 illustrate a method of manufacturing the thin-walled, elastic sheath 54. The method uses a sheet 70 of elastomeric material, such as a polyurethane, that contains friction-reducing additives or slip agents, such as wax, oil, silicon or silica. In the illustrated embodiment, the sheet 70 has an initial thickness of about 0.042 inches, although the thickness of the sheet 70 can vary based on the desired length and thickness of the sheath 54 being formed. The sheet 70 of the elastomeric material is retained on a substantially flat support 72 having a central opening 74 extending therethrough. A portion of the elastomeric sheet 70 above the central opening is heated by a conventional heating device to a selected malleable temperature to form a malleable, heated portion 75 of the sheet 70. A forming tool 76 is then pressed into the heated portion 75 in a direction substantially normal to the plane of the sheet 70, illustrated by the direction I. In the illustrated embodiment, the forming tool 76 has a generally circular cross-section. The forming tool 76, however, could also have an oval, polygonal or other suitable cross-sectional shape. As the forming tool 76 is pressed into the heated portion 75, the elastomeric sheet 70 stretches beyond its modulus of elasticity to form an elongated, thin-walled protrusion 78 (FIG. 8). The protrusion 78 will eventually become all or a portion of the sheath 54, as the excess material from the elastomeric sheet 70 is trimmed from the protrusion 78.

As illustrated in FIG. 8, the protrusion 78 has an open proximal portion 80, a closed distal portion 82 spaced away from the open proximal portion 80, and sidewalls 84 extending between the proximal and distal portions. The closed distal portion 82 and the sidewalls 84 define an interior 86 of the protrusion 78. As the forming tool 76 is moved in the direction I, the interior 86 of a conforming portion 87 at the distal portion 82 of the protrusion 78 begins to closely conform to the outer shape of the forming tool. As the forming tool 76 is moved further in the direction I, the conforming portion 87 of the protrusion 78 progressively conforms to more of the length of the forming tool 75. The forming tool 76 is moved in the direction I until the length of the conforming portion 87 of the protrusion 78 is at least as long as the desired length of the elastic sheath 54 being formed. The elastic sheath 54 can be as long as the insertion tube 52 for which it will be used, or it can be shorter than the insertion tube 52 (FIG. 5) to allow the elastic sheath 54 to be stretched axially over the insertion tube when installed. The forming tool 76 can be stopped when the conforming portion 87 is at the desired length, or it can be moved further if desired to reduce the thickness of the sidewalls 84. The thickness of the sidewalls 84 in one embodiment is in the range of approximately 0.002 to 0.009 inches, inclusive, and preferably in the range of approximately 0.002 to 0.006 inches, inclusive, or can be thinner than 0.002 inches. After the elongated, thin-walled conforming portion 87 of the protrusion 78 is formed to a desired length and thickness, the protrusion is allowed to cool to a temperate at which the elastomeric material is no longer malleable.

After the protrusion 78 has cooled, the forming tool 76 is removed from the protrusion 78 and the protrusion is cut to separate the elastic sheath 54 from the elastomeric sheet 70. The distal portion 82 of the protrusion 78 can be left on what is now the elastic sheath 54, or it can be removed and replaced with an end cap 64 (FIG. 6). If needed during manufacturing, the sheath 54 can then be trimmed at the distal end to the desired length before attaching the end cap.

The elastomeric material used with the above embodiment of the present invention is a thermoplastic, elastomeric material, such as polyurethane containing one or more conventional slip agents, such as wax, oil, silicone or silica. Such slip agents are commonly used in the field of elastomeric materials, and an individual having ordinary skill in such an art will understand how to treat the elastomeric material to provide the desired properties for reduced friction. The treated elastomeric material allows for small diameter, thin-walled elastic medical components that can be easily, inexpensively, and quickly manufactured.

Embodiments of the present invention have a number of advantages over the sheaths of the prior art and the methods of making such sheaths. Because the elastomeric material is allowed to cool on the forming tool, the forming tool prevents the sheath from collapsing and sticking to itself while the elastomeric material is heated and tacky. This is an improvement over traditional extruded sheaths that could collapse during forming. If the sheath collapsed while the elastomeric material was hot and tacky, the sheath could be ruined.

Also, because the elastic sheath 54 is made from an elastomeric material treated with slip agents, the sheath can be formed with a relaxed inner diameter only slightly larger than an outside diameter of the insertion tube 52 and still be easily installed. The slip agents allow the insertion tube to be easily inserted into the elastic sheath 54 without the distal end 56 of the insertion tube 52 binding, catching, or excessively distorting the elastic sheath 54 during installation. Thus the need for baggy sheaths can be eliminated. The need for additional equipment and features previously used to radially expand the tight-fitting, elastic sheath during installation are also eliminated.

Further, because the elastic sheath 54 is made from an elastomeric material, the diameter and wall thickness of the elastic sheath 54 decrease as the sheath is stretched axially over the insertion tube. Accordingly, the overall cross-section of the sheathed insertion tube may be minimized, thereby reducing the pain or discomfort experienced by a patient. Stretching the sheath also creates an axial restoring force in the elastomeric material which retains the end cap 64 at the distal end 58 of the elastic sheath 54 in contact and alignment with the distal end 56 of the insertion tube 52.

While the elastic sheath 54 and the method of making the sheath are discussed herein with reference to an endoscope 50, the method of the present invention is equally applicable to other medical components. For example, the medical component in alternate embodiments can be a catheter, optical imaging medical equipment, and non-optical imaging medical equipment.

Figure 9:
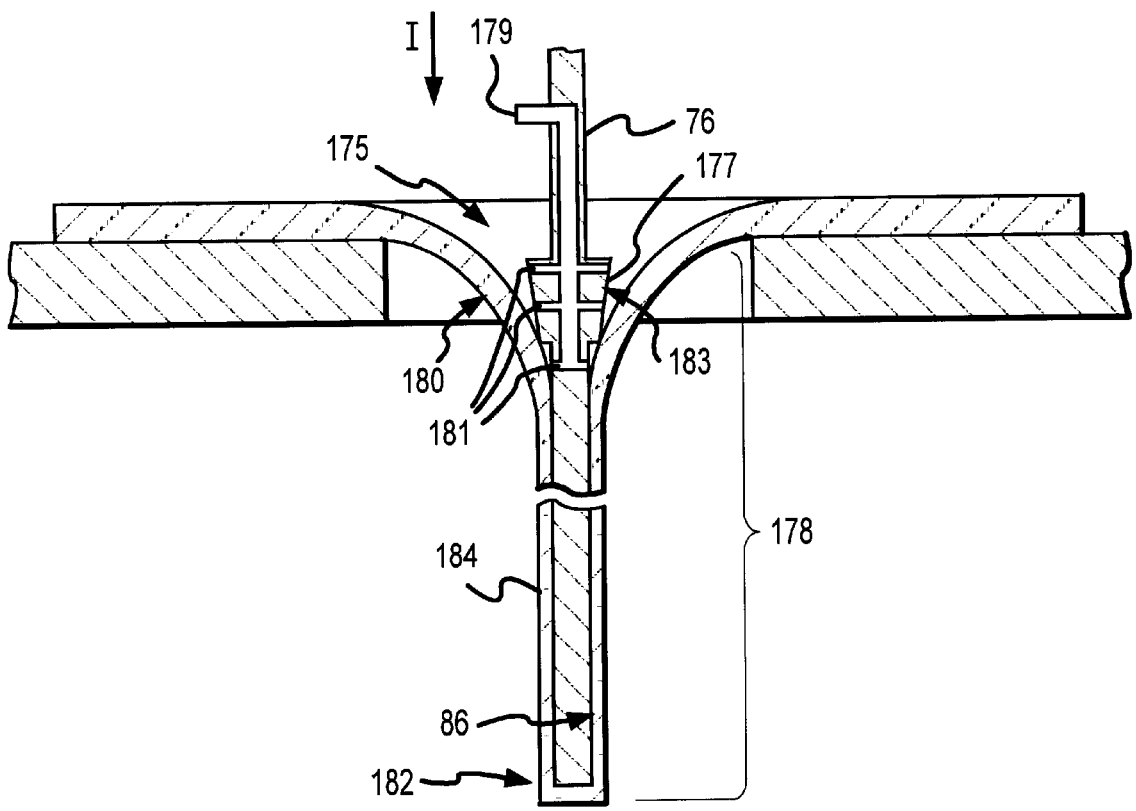
FIG. 9 is a cross-sectional view of another forming tool, a sheet of elastomeric material and a support structure according to another embodiment of the present invention after the sheath has been partially formed.
Figure 10:
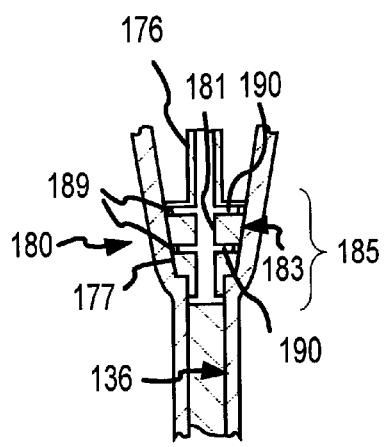
FIG. 10 is a partial, cross-sectional view of a proximal portion of the sheath of FIG. 9 after the sheath has been fully formed.

FIGS. 9 and 10 illustrate an alternate embodiment of the method of the present invention. In this particular embodiment, best illustrated in FIG. 9, the forming tool 176 has a tapered annular portion 177 at a point selected to correspond to a proximal end 180 of the elastic sheath 178. The annular portion 177 is provided in this embodiment in order to form an integral collar 185 (FIG. 10) at the sheath's proximal end 180. After the forming tool 176 is moved to a point at which the elastomeric sheet's malleable heated portion 175 has at least partially conformed to the annular portion 177, a radially inward force is applied to the sidewalls 184 to force the sidewalls against the annular portion 177. In the illustrated embodiment, the radially inward force is applied to the sidewalls 184 by a vacuum source (not shown) attached to a vacuum port 179 in the forming tool 176. A partial vacuum is applied to the interior 186 of the sheath 178 via a number of ports 181 in the forming tool 176. In an alternate embodiment, a radially inward force is applied by pressing on the exterior of the sheath's sidewalls. As illustrated in FIG. 10, the forming tool's annular portion 177 has a plurality of passages 190 into which a portion of the sidewalls 184 is drawn when the radially inward force is applied. The passages 190 are shaped and sized to form retention members 189 in the proximal end 180 of the sheath 178 that releasably engage the distal end of the endoscope control body (not shown). In one embodiment, the passages 190 are shaped into annular grooves extending about the annular portion 177. In that embodiment, the retention members 189 are formed into annular inward projections. Thus, the elastic sheath 178 is formed with an integral proximal fitting used for retaining the sheath on the endoscope in the installed position. In the illustrated embodiment, the retention members 189 are annular in shape and have rectilinear cross-sections. The retention members 189, however, can have other shapes and sizes.

As described above, the cooled, elastic sheath 178 is then removed from the forming tool 176 and the elastic sheath 178 is trimmed or cut near the proximal end 180 to remove excess material from the sheath 178. In the exemplary embodiment, the sheath's distal end 182 may also be trimmed, and an end cap, such as that illustrated in FIGS. 5 and 6, is adhered or otherwise connected to the distal end 182. In one embodiment, the sheath's distal end 182 extends over the outside of the endcap and is sealably bonded in place. In an alternate embodiment, the sheath's distal end 182 is sealably bonded to the inside of the endcap. The sheath 178 is then ready for use with an endoscope to perform a selected endoscopic procedure without contaminating the endoscope's insertion tube.

Figure 11:
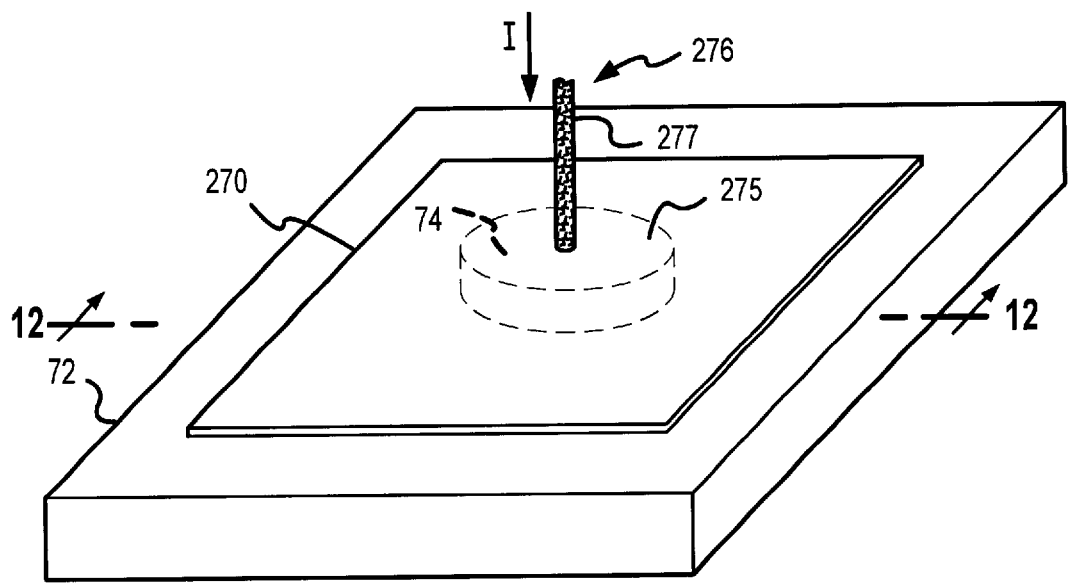
FIG. 11 is an isometric view of a sheet of sheath material positioned below a forming tool in accordance with another embodiment of the invention.
Figure 12:
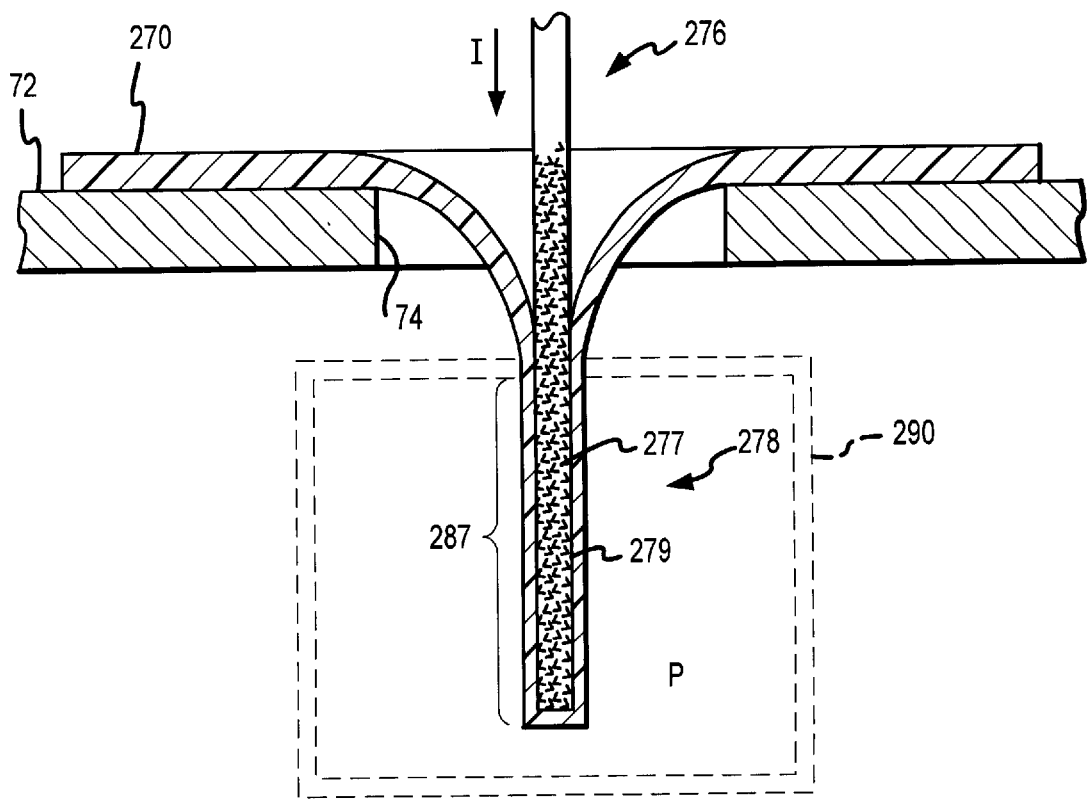
FIG. 12 is an enlarged, partial cross-sectional view of the forming tool and sheet of sheath material of FIG. 11 taken along line 12—12.

FIG. 11 is an isometric view of a sheet of sheath material 270 positioned below a forming tool 276 in accordance with another embodiment of the invention. FIG. 12 is an enlarged, partial cross-sectional view of the forming tool 276 of FIG. 11 engaged with the sheet of sheath material 270. In this embodiment, the forming tool 276 includes a textured portion 277. The sheet of sheath material 270 is retained on a support 72 having a central opening 74 as described above. A portion of the sheet of sheath material 270 proximate the central opening 74 is heated to form a malleable heated portion 275. Alternately, depending upon the material properties of the sheet of sheath material 270, the entire sheet may be heated.

As best shown in FIG. 12, the textured portion 277 of the forming tool 276 is not smooth. Rather, the textured portion 277 is an uneven, non-smooth portion that includes a plurality of surface features. The surface features may be distributed over the textured portion 277 in any desired manner or configuration, including, for example, random spacing, uniform spacing, or non-uniform spacing. Also, it should be understood that the surface features may be raised features that project above a nominal surface level of the forming tool 276, or may be lowered features that project below the nominal surface level (such as, for example, in a porous portion), or may include both raised and lowered features.

In operation, the forming tool 276 may be pressed into the heated portion 275 in a direction substantially normal to the plane of the sheet 270, denoted by the arrow I (FIGS. 11 and 12). As the forming tool 276 presses into the heated portion 275, the sheet of sheath material 270 stretches to form an elongated portion 278. A conforming portion 287 of the elongated portion 278 has an inner surface 279 that contacts the textured portion 277 of the forming tool 276. The inner surface 279 may thereby conform and adapt to the textured portion 277 so that the inner surface 279 becomes textured. After the conforming portion 287 is formed to the desired length and thickness (as described above), the conforming portion 287 may be allowed to cool to a temperature at which the sheet of sheath material 270 is no longer malleable, and the forming tool 276 may be withdrawn from the elongated portion 278. The conforming portion 287 may then be processed in the manner set forth above to form an embodiment of a sheath 254 including an elongated, tubular portion having a textured interior surface.

It should be understood that for various sheath materials, it may not be desirable or necessary to cool the sheet of sheath material 270 prior to withdrawing the forming tool 276. For example, for some types of surface features (e.g., those formed by a deeply porous textured portion), and for some sheath materials (e.g., inelastic, plastic, or thermosetting materials), it may be desirable to remove the forming tool 276 from the elongated portion 278 prior to cooling the conforming portion 287. Alternately, the temperature of the sheet of sheath material 270 may be partially cooled so that the sheet remains flexible and compliant, but the interior surface 279 retains its texture, as the forming tool 276 is removed.

Because prior art methods of forming sheathes utilize a mandrel having an approximately smooth surface, the inner surface of the prior art sheath is also relatively smooth. Typically, mandrels used to form endoscopic sheaths in accordance with the prior art have surface finishes resulting from ordinary machining operations that may be characterized by a surface roughness average value R of approximately 0.000016 inches (0.4 microns) to 0.000125 inches (3.20 microns). The surface roughness average value R is a standard engineering parameter defined as a number which equals the arithmetical average deviation of the minute surface irregularities from a hypothetical perfect surface (see, for example, Marks' Standard Handbook for Mechanical Engineers, Ninth Edition, p. 13–79). Therefore, the roughness and irregularities of the surfaces of mandrels in accordance with the prior art are approximately imperceptible to the touch and to the unassisted eye.

In contrast, the surface features of the textured portion 277 of the forming tool 276 (and thus the textured inner surface 279) are generally perceptible to the touch and to the unassisted eye. Although the size and shape of the surface features of the textured portion 277 (and the textured inner surface 279) may vary greatly depending upon, for example, the sheath materials used, the size of the sheath, or the intended use of the sheath, in some embodiments, the average heights of the surface features may be approximately 0.005 inches (125 microns) or greater. In a preferred embodiment, the average height or depression of the surface features of the forming tool 276 (and thus the textured inner surface 279) is approximately 0.03 inches (0.75 mm). It may be noted that the surface features may vary in height, shape, pattern density, and other characteristics.

The sheath 254 having a textured interior surface may advantageously improve the process of installing and removing the sheath 254 from an endoscopic insertion tube. Typically, endoscope insertion tubes may be adversely affected by such factors as reprocessing, operator mishandling, and normal wear which may cause material changes or dimensional changes of the device. For example, low durometer (soft) plastic materials used to construct flexible insertion tubes have been proven to degrade when repeatedly exposed to reprocessing chemicals such as, for example, Glutaraldehyde, hydrogen peroxide, and ethylene oxide. Such chemicals may cause insertion tube materials to crack, swell, and become tacky, making the process of installing and removing a sheath more difficult. The sheath 254 having a textured interior surface in accordance with an embodiment of the invention, however, may reduce the contact area between the sheath 254 and the insertion tube. Because the contact area is reduced, the friction between the sheath 254 and insertion tube may also be reduced. Consequently, the sheath 254 may be installed and removed more easily and quickly compared with conventional sheaths having a smooth interior surface.

For some sheath materials, the inner surface 279 of the elongated portion 278 may not readily conform to the textured portion 277 of the forming tool 276. Thus, it may be desirable to apply a pressure differential to the conforming portion 287 to force the inner surface 279 against the textured portion 277 thereby causing the inner surface 279 to more readily conform to the textured portion 277. In one embodiment, a method includes forming the pressure differential by reducing the pressure within the conforming portion 287. For example, the forming tool 276 may be modified to include an integral collar 185 (as shown in FIG. 10) having a plurality of ports 181 fluidly coupled with a vacuum port 179. As described above, a vacuum source may be applied to the vacuum port 179 to reduce the pressure within the sheath 254, creating an inward force that presses the inner surface 279 against the textured portion 277. Alternately, a pressure vessel 290 may be disposed about the conforming portion 287, and a conforming pressure P may be generated within the pressure vessel 290, thereby creating an inward force that presses the inner surface 279 against the textured portion 277.

Furthermore, it should be noted that, after the conforming portion 287 having a textured inner surface 279 is formed, the forming tool 276 may not be easily removable from the conforming portion 287. The surface features of the inner surface 279 may become interlocked with the surface features of the textured portion 277, preventing the forming tool 276 from being withdrawn from the conforming portion 287. Therefore, a method for forming the sheath 254 may include creating a disengagement pressure differential that disengages the textured inner surface 279 from the textured portion 277. In one embodiment, the forming tool 276 may include the integral collar 185 described above (FIG. 10). The vacuum port 179 may be coupled to a pressure source (e.g., a pump) to increase the pressure within the conforming portion 287, thereby creating an outward force that drives the inner surface 279 away from the textured portion 277, thereby disengaging the conforming portion 287 from the forming tool 276. Alternately, a pressure vessel 290 may be disposed about the conforming portion 287, and a reduced pressure (or "vacuum") P may be generated within the pressure vessel 290, thereby creating an outward force that drives the inner surface 279 away from the textured portion 277.

Figure 13:
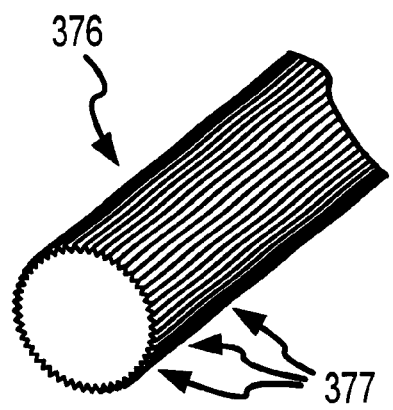
FIG. 13 is an isometric view of a patterned forming tool for forming a sheath in accordance with an alternate embodiment of the invention.
Figure 14:
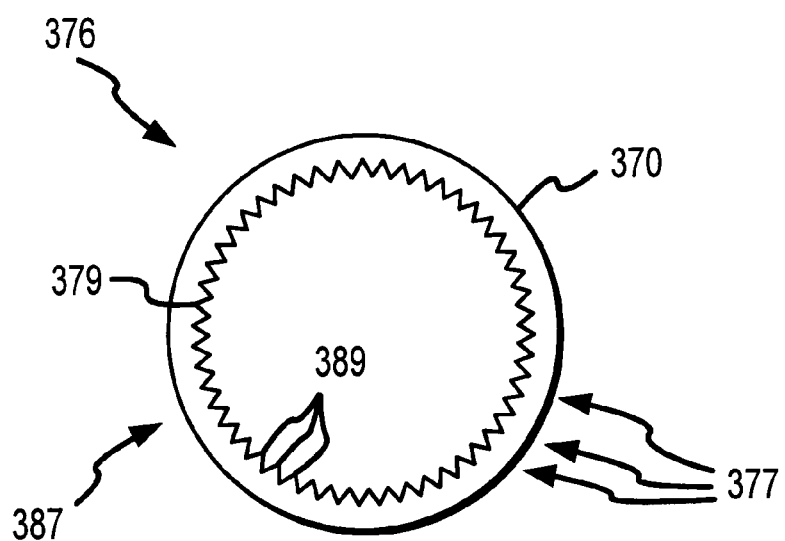
FIG. 14 is an axial cross-sectional view of the patterned forming tool of FIG. 13 engaged with a conforming portion of a sheet of sheath material.

FIG. 13 is an isometric view of a patterned forming tool 376 for forming a sheath 354 in accordance with an alternate embodiment of the invention. FIG. 14 is an axial cross-sectional view of the patterned forming tool 376 of FIG. 13 engaged with a conforming portion 387 of a sheet of sheath material 370. The forming tool 376 includes an outer surface having a plurality of longitudinal grooves 377 disposed therein. As best shown in FIG. 14, when the forming tool 376 is pressed into a sheet of sheath material 370, an inner surface 379 of the conforming portion 387 adapts to the grooves 377 so that the inner surface 379 becomes longitudinally grooved. Ridges 389 are thereby formed on the inner surface 379. The conforming portion 387 may then be processed as described above to create the sheath 354 having the longitudinally-grooved inner surface 379.

Although the patterned forming tool 376 is shown in FIGS. 13 and 14 as being patterned with longitudinal grooves 377, a variety of forming tools featuring a variety of surface patterns may be used. For example, forming tools having spiral grooves, circumferential grooves, crosshatching grooves, pores, dimples, or any other desired pattern may be used. Furthermore, in place of grooves, forming tools having raised features may also be used.

The method of forming a sheath 354 using a patterned forming tool 376 advantageously provides a patterned inner surface 379 which may reduce the friction between the inner surface and the endoscopic insertion tube. When the insertion tube is inserted into the sheath 354, the ridges 389 may contact the outer surface of the insertion tube, thereby reducing the amount of contact area between the sheath 354 and insertion tube. Because the contact area is reduced compared with sheaths having smooth inner walls, the sheath 354 having the patterned inner surface 379 may be more easily installed and removed. Thus, the sheath 354 may be more easily and efficiently installed and removed from the insertion tube, and the user's satisfaction may be increased.

Figure 15:
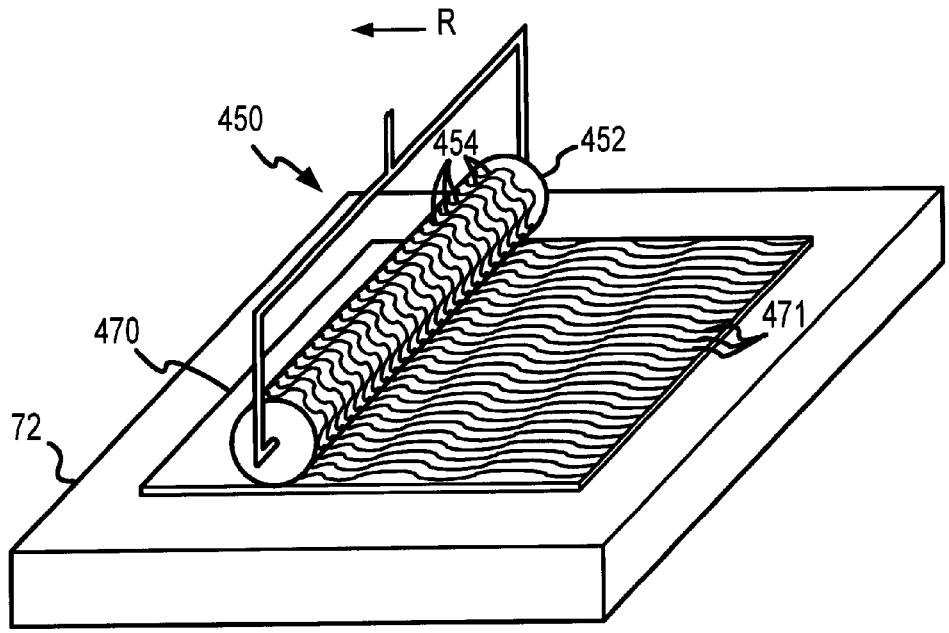
FIG. 15 is an isometric view of a sheet of sheath material engaged with a patterning tool in accordance with another embodiment of the invention.

FIG. 15 is an isometric view of a sheet of sheath material 470 engaged with a patterning tool 450 in accordance with another embodiment of the invention. The patterning tool 450 includes a roller 452 having a plurality of ridges 454. The sheet of sheath material 470 may be made malleable or deformable, such as by heating or applying solvents, and the roller 452 may be pressed against the sheet and rolled in a direction R across the face of the sheet. The ridges 454 press into the sheet and create a plurality of channels 471 in the sheet. The sheet of sheath material 470 may then be processed according to one of the methods described above to form a sheath 454 having a channeled inner surface 479. For example, a smooth-walled forming tool 76 (FIGS. 7 and 8) may be pressed into the sheet of sheath material 470, forming an elongated portion 478 having the channeled inner surface 479.

It may be understood that the sheet of sheath material 470 may be patterned using a wide variety of patterning tools, including presses, dies, stamps, lathes, milling machines, or other suitable devices. Also depending upon the material properties of the sheet, and the patterning tool employed, it may not be necessary to make the sheet malleable prior to patterning. For example, an inelastic or plastic material may be patternable using a mill or press without heating the sheet, or otherwise making the sheet malleable. Furthermore, the sheet of sheath material may be heated to a first temperature for patterning with a patterning tool, and then cooled to a relatively lower temperature for pressing with the forming tool so that the pre-patterned channels on the sheet are not lost during the process of forming the elongated portion 378. Finally, it is understood that sheet material may also be patterned or textured by either the calendaring or casting process by which it is originally formed.

The method of forming the sheath 454 from a pre-patterned sheet of sheath material 470 may provide advantages over alternate methods of forming sheaths having patterned inner surfaces. Because the sheet of sheath material is pre-patterned, it may be easier to extract the forming tool from within the conforming portion during manufacture. Because the patterned inner surface 479 is less likely to interlock with the surface of the smooth-walled forming tool 79 (FIG. 7), the forming tool 79 may be more easily withdrawn, and the need for applying a disengagement pressure differential may be reduced or eliminated. Thus, because the sheet of sheath material 470 is pre-patterned using the patterning tool 450, it is less likely that the forming tool will require an integral collar 185 (FIGS. 9 and 10) or other system for increasing the pressure within the conforming portion 478 to disengage the channeled inner surface 479 from the forming tool. Overall, the apparatus required to manufacture the sheath 454 may be simplified, and the method of manufacture may be more efficient, than alternate methods.

Figure 16:
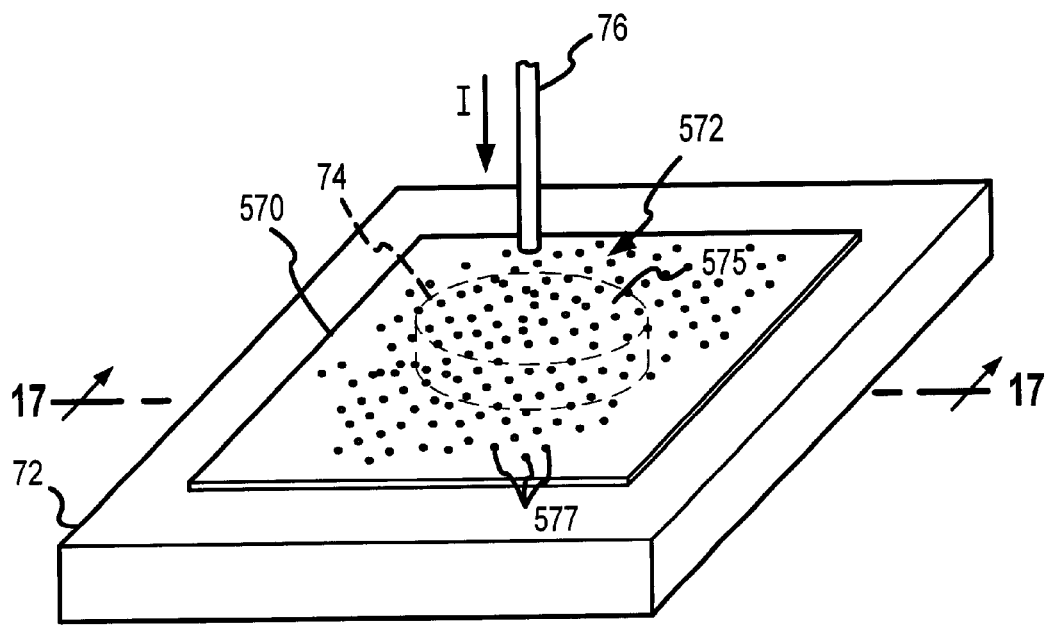
FIG. 16 is an isometric view of a sheet of sheath material treated with a slip agent and positioned below a forming tool in accordance with yet another embodiment of the invention.
Figure 17:
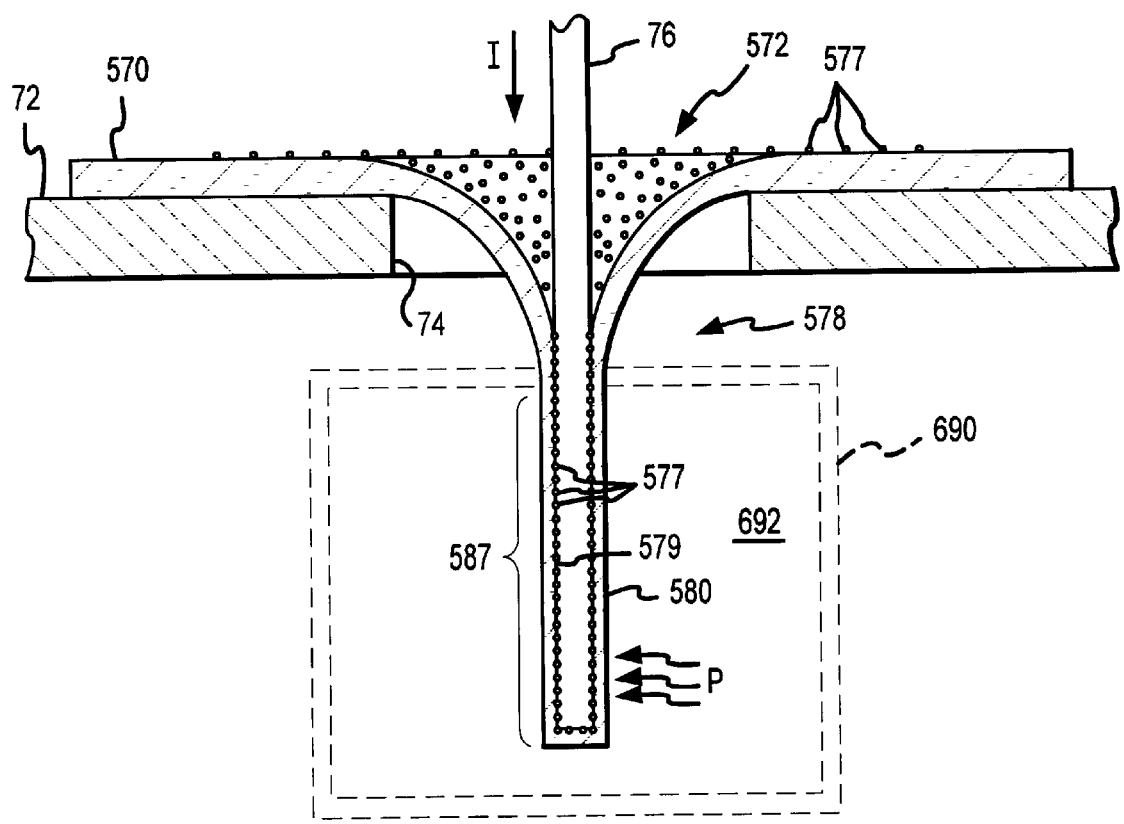
FIG. 17 is an enlarged, partial cross-sectional view of the forming tool engaged with the sheet of sheath material of FIG. 16 taken along line 17—17.

FIG. 16 is an isometric view of a sheet of sheath material 570 treated with a slip agent 572 and positioned below a forming tool 76 in accordance with yet another embodiment of the invention. FIG. 17 is an enlarged, partial cross-sectional view of the forming tool 76 engaged with the sheet of sheath material 570 of FIG. 16 taken along line 17—17. In this embodiment, the slip agent 572 includes a plurality of granules (or particles) 577. The granules 577 may be distributed on the surface of the sheet of sheath material 570. As set forth above, the sheet of sheath material 570 may be retained on a support 72 having a central opening 74. A portion of the sheet 570 proximate the central opening 74 is treated (e.g., heated, exposed to solvents, etc.) to form a malleable portion 575. Alternately, the entire sheet 570 may be treated.

In operation, the forming tool 76 may be pressed into the malleable portion 575 in a direction substantially normal to the plane of the sheet 570, denoted by the arrow I (FIGS. 16 and 17). As the forming tool 76 presses into the malleable portion 575, the sheet 570 stretches to form an elongated portion 578 (FIG. 17). A conforming portion 587 of the elongated portion 578 has an inner surface 579 that presses some of the granules 577 against the forming tool 76 as the forming tool is pressed into the malleable portion 575 of the sheet 570. One may note that in alternate embodiments, a textured forming tool 276 (FIGS. 11 and 12), or a patterned forming tool 376 (FIGS. 13 and 14), may be used.

Figure 18:
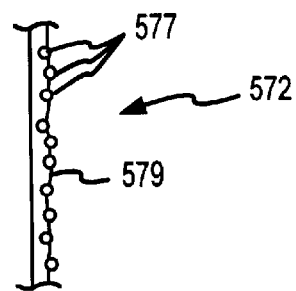
FIG. 18 is an enlarged, partial cross-sectional view of an inner surface treated with the slip agent after engagement with the forming tool of FIG. 17.

FIG. 18 is an enlarged, partial cross-sectional view of the inner surface 579 treated with the slip agent 572 after engagement with the forming tool 76 of FIG. 17. As shown in FIG. 18, the granules 577 may become partially or wholly embedded into the inner surface 579. Alternately, some or all of the granules 577 may remain on top of the inner surface 579. After the conforming portion 587 is formed to the desired length and thickness (as described above), the conforming portion 587 may be cooled (or otherwise made non-malleable), and the forming tool 76 may be withdrawn from the elongated portion 578. The conforming portion 587 may then be processed in the manner set forth above to form an embodiment of a sheath 554 having an interior surface 579 treated with the slip agent 572.

It should be understood that a variety of powdered or granular slip agents 572 may be used, including, for example, cornstarch, silica, materials sold under the trademark TEFLON®, or other suitable materials. Also, the granules 577 may be partially or wholly embedded in the surface of the sheet 570 prior to engaging the sheet 570 with the forming tool 76. For example, the granules 577 may be pressed against the surface of the sheet 570 using a rolling tool (FIG. 15), a press, or other suitable device, or may be caste or otherwise integrally formed into the surface during manufacture of the sheet 570. Furthermore, one may note that various liquid slip agents may be used, including, for example, oils, silicone, liquefied wax, or other suitable agents. Such liquid slip agents may remain on top of the inner surface 579, or may be partially or wholly absorbed into the inner surface 579 during the manufacturing process.

An advantage of the sheath 554 having an inner surface 579 treated with the slip agent 572 is that the process of installing or removing the sheath from an endoscopic insertion tube may be improved. The slip agent 572 may advantageously reduce the surface friction of the inner surface 579, allowing the sheath 554 to be slid onto and off of the insertion tube more easily. For the embodiment of the slip agent 572 having granules 577, the granules 577 which become partially embedded within the inner surface 579 may cause the inner surface 579 to remain spaced apart from the outer surface of the insertion tube in the localized area of the embedded granule, reducing the contact area between the inner surface 579 and the insertion tube. Loose granules 577 which remain on top of the inner surface 579 may also act as spacers which space apart the inner surface 579 from the insertion tube, and may also roll or slide along these respective surfaces, acting as small bearings which further reduce the friction between the inner surface 579 and the insertion tube. Because the sheath 554 may be more easily installed and removed from the insertion tube, medical procedures may be more efficiently conducted, and user satisfaction with the sheath 554 may be improved.

In some applications, it may be advantageous to apply a slip agent or other substance to an outer surface 580 of a sheath 654. For example, as shown in FIG. 17, a vessel 690 may be disposed about the conforming portion 587 of the sheet of sheath material 570. The vessel 690 may contain a treating agent 692, such as a slip agent (e.g., oil, silica, wax, cornstarch, etc.), a medication (e.g., an anesthetic, antibiotic, anti-inflammatory, etc.), or any other desired material. The vessel 690 may be pressurizable so that the treating agent 692 may be pressured to an elevated pressure level P to force the treating agent 692 into contact with the outer surface 580, as well as to force the inner surface 579 into contact with the slip agent 572 as described above. Alternately, like the slip agent 572 described above, the treating agent 692 may be applied to the outer surface 580 prior to engaging the sheet of sheath material 570 with the forming tool 76, thereby eliminating the vessel 690.

The sheath 654 having a treating agent 692 on an outer surface 580 may have improved physical or chemical characteristics. For example, the treating agent 692 may include a slip agent that makes it easier to introduce a sheathed endoscope into a patient's body. Alternately, the treating agent 692 may include a medication, such as a topical anesthetic to make the procedure less uncomfortable for the patient, or other various drugs that would treat a medical condition within the patient's body. Therefore, a sheath 654 having a treating agent 692 thereon may provide beneficial results, and may improve the patient's health and satisfaction with the medical procedure.

From the foregoing it will be appreciated that, although specific embodiments of the invention have been described herein for purposes of illustration, various modifications may be made without deviating from the spirit and scope of the invention. Also, although the various embodiments of the invention have been described as being used to form complex components, it will be understood that relatively simple components may also be formed in accordance with the invention. Accordingly, the invention is not limited except as by the appended claims.

What is claimed is:

1. A sheath adapted for use with an endoscopic insertion tube, comprising:
    an elongated, tubular portion formed of an impermeable polymeric material and having an inner surface substantially surrounding a volume adapted to receive and extend substantially about the insertion tube, at least a portion of the inner surface including a textured surface having a plurality of surface features formed of the impermeable polymeric material, the tubular portion further having a smooth outer surface opposite from the inner surface.

2. The sheath according to claim 1 wherein the tubular portion comprises an elastic tubular portion.

3. The sheath according to claim 1 wherein the surface features of the textured surface comprise non-uniformly spaced surface features.

4. The sheath according to claim 1 wherein the surface features of the textured surface comprise longitudinally disposed grooves.

5. The sheath according to claim 1, further comprising a fitting attached to a proximal end of the tubular portion.

6. The sheath according to claim 1 wherein at least some of the inner surface includes a slip agent.

7. The sheath according to claim 6 wherein the slip agent is at least partially embedded in the inner surface.

8. The sheath according to claim 6 wherein the slip agent is disposed on the inner surface.

9. The sheath according to claim 6 wherein the slip agent comprises a granular slip agent.

10. The sheath according to claim 6 wherein the slip agent comprises a liquid slip agent.

11. The sheath according to claim 6 wherein the slip agent comprises an oil.

12. The sheath according to claim 6 wherein the slip agent comprises a silica.

13. A sheath adapted for use with an endoscopic insertion tube, comprising:
    an elongated, tubular portion formed of an impermeable polymeric material and having an inner surface substantially surrounding a volume adapted to receive and extend substantially about the insertion tube, at least a first portion of the inner surface including a slip agent and at least a second portion of the inner surface including a textured surface having a plurality of surface features formed of the impermeable polymeric material, the tubular portion further having a smooth outer surface opposite from the inner surface.

14. The sheath according to claim 13 wherein the first and second portions at least partially overlap.

15. The sheath according to claim 13 wherein at least some of the slip agent is partially embedded in the inner surface.

16. The sheath according to claim 13 wherein at least some of the slip agent is disposed on the inner surface.

17. The sheath according to claim 13 wherein the slip agent comprises a granular slip agent.

18. The sheath according to claim 13 wherein the slip agent comprises a liquid slip agent.

19. The sheath according to claim 13 wherein the tubular portion comprises an elastic tubular portion.

20. The sheath according to claim 19 wherein the second portion is coextensive with the first portion.

21. The sheath according to claim 19 wherein the surface features of the textured surface comprise non-uniformly spaced surface features.

22. The sheath according to claim 19 wherein the surface features of the textured surface comprise longitudinally disposed grooves.

23. The sheath according to claim 13, further comprising a fitting attached to a proximal end of the tubular portion.

24. A sheath adapted for use with an endoscopic insertion tube, comprising:

an elongated, tubular portion formed of an impermeable polymeric material and having an inner surface substantially surrounding a volume adapted to receive and extend substantially about the insertion tube, and an outer surface opposite from the inner surface, at least a portion of the outer surface including a treating agent comprising a medication, wherein the medication comprises an anti-inflammatory medication.

25. The sheath according to claim 24 wherein the tubular portion comprises an elastic tubular portion.

26. The sheath according to claim 24 wherein the treating agent includes a slip agent.

27. The sheath according to claim 26 wherein at least some of the slip agent is partially embedded in the outer surface.

28. The sheath according to claim 26 wherein the slip agent comprises a granular slip agent.

29. The sheath according to claim 26 wherein the slip agent comprises a liquid slip agent.

30. The sheath according to claim 24 wherein the medication additionally comprises an anesthetic.

31. A method of forming a sheath adapted to be engageable with an endoscopic insertion tube, comprising:

providing a sheet of sheath material;

applying a slip agent to a surface of the sheet; and after or simultaneously with applying the slip agent to the surface of the sheet, forming the sheet into a tubular sheath adapted to at least partially receive the endoscopic insertion tube.

32. The method according to claim 31 wherein providing a sheet of sheath material comprises providing a sheet of elastomeric material.

33. The method according to claim 31 wherein applying a slip agent to a surface of the sheet comprises applying a slip agent to a first surface of the sheet, the first surface forming an inner surface of the tubular sheath.

34. The method according to claim 31 wherein applying a slip agent to a surface of the sheet comprises applying a slip agent to a first surface of the sheet, the first surface forming an outer surface of the tubular sheath.

35. The method according to claim 31 wherein applying a slip agent to a surface of the sheet includes partially embedding a plurality of granules into the surface of the sheet.

36. The method according to claim 31 wherein applying a slip agent to a surface of the sheet includes partially absorbing a liquid slip agent into the surface of the sheet.

37. The method according to claim 31 wherein forming the sheet into a tubular sheath includes partially embedding at least a portion of the slip agent into the surface of the sheet.

38. The method according to claim 31 wherein providing a sheet of sheath material comprises providing a sheet of elastomeric sheath material, and wherein forming the sheet into a tubular sheath includes forming a malleable portion of the sheet; and pressing an elongated forming tool into the malleable portion of the sheet.

39. The method according to claim 31 wherein forming the sheet into a tubular sheath includes pressing an elongated, textured forming tool into a conforming portion of the sheet.

40. The method according to claim 31 wherein providing a sheet of sheath material comprises providing a sheet of textured sheath material.

41. The method according to claim 31 wherein forming the sheet into a tubular sheath includes pressing an elongated, textured forming tool into a conforming portion of the sheet; and applying a conforming pressure against a backside surface opposite from the conforming portion of the sheet.

42. The method according to claim 31 wherein forming the sheet into a tubular sheath includes pressing an elongated, textured forming tool into a conforming portion of the sheet; and applying a disengaging pressure against the conforming portion of the sheet.

43. A method of forming a sheath adapted to be engageable with an endoscopic insertion tube, comprising:

providing a sheet of sheath material;

forming the sheet into a tubular sheath sized and shaped to at least partially receive the endoscopic insertion tube; and simultaneously with forming the sheet into a tubular sheath, texturing a surface of the sheet of sheath material that forms an inner surface of the tubular sheath.

44. The method according to claim 43 wherein providing a sheet of sheath material comprises providing a sheet of elastomeric material.

45. The method according to claim 43 wherein forming the sheet into a tubular sheath includes pressing an elongated, textured forming tool into a conforming portion of the sheet.

46. The method according to claim 43 wherein texturing a surface of the sheet of sheath material that forms an inner surface of the tubular sheath includes pressing an elongated, textured forming tool into a conforming portion of the sheet.

47. The method according to claim 43 wherein texturing a surface of the sheet of sheath material that forms an inner surface of the tubular sheath includes forming longitudinal grooves within the surface of the sheet of sheath material.

48. The method according to claim 43 wherein texturing a surface of the sheet of sheath material that forms an inner surface of the tubular sheath includes texturing a surface of the sheet of sheath material by calendering the surface.

49. The method according to claim 43 wherein texturing a surface of the sheet of sheath material that forms an inner surface of the tubular sheath includes texturing a surface of the sheet of sheath material by casting the surface.

50. The method according to claim 43 wherein forming the sheet into a tubular sheath includes forming a malleable portion of the sheet;

pressing an elongated forming tool into the malleable portion of the sheet; and stretching the malleable portion with the forming tool until a conforming portion of the sheet is conformed to the forming tool.

51. The method according to claim 43 wherein forming the sheet into a tubular sheath includes pressing an elongated, textured forming tool into a conforming portion of the sheet; and applying a conforming pressure against a backside surface opposite from the conforming portion of the sheet.

52. The method according to claim 43 wherein forming the sheet into a tubular sheath includes pressing an elongated, textured forming tool into a conforming portion of the sheet; and applying a disengaging pressure against the conforming portion of the sheet.

53. The method according to claim 43, further comprising applying a slip agent to a first surface of the sheet.

54. The method according to claim 53 wherein applying a slip agent to a first surface of the sheet comprises applying a slip agent to the surface that forms the inner surface of the tubular sheath.

55. The method according to claim 53 wherein applying a slip agent to a first surface of the sheet comprises applying a slip agent to a surface that forms an outer surface of the tubular sheath.

56. The method according to claim 53 wherein forming the sheet into a tubular sheath includes partially embedding at least some of the slip agent into the surface of the sheet.

57. A method of forming a sheath adapted to be engageable with an endoscopic insertion tube, comprising:
providing a sheet of impermeable polymeric sheath material;
forming the sheet into a tubular sheath sized and shaped to at least partially receive the endoscopic insertion tube; and
applying a treating agent including a medication to a surface of the sheet of sheath material that forms an outer surface of the tubular sheath, wherein applying a treating agent to a surface of the sheet of sheath material comprises applying a treating agent to a surface of the sheet of sheath material simultaneously with forming the sheet into a tubular sheath.

58. The method according to claim 57 wherein applying a treating agent to a surface of the sheet of sheath material that forms an outer surface comprises applying an anti-inflammatory to a surface of the sheet of sheath material that forms an outer surface.

59. The method according to claim 57 wherein applying a treating agent to a surface of the sheet of sheath material that forms an outer surface comprises applying an anesthetic to a surface of the sheet of sheath material that forms an outer surface.

60. The method according to claim 57 wherein applying a treating agent to a surface of the sheet of sheath material that forms an outer surface comprises partially embedding a treating agent into a surface of the sheet of sheath material that forms an outer surface.

61. An endoscope assembly, comprising:
an endoscope including an elongated insertion tube; and
a sheath having an elongated, tubular portion at least partially encapsulating the insertion tube, the tubular portion further having an inner surface proximate the insertion tube, at least a portion of the inner surface including a slip agent, wherein at least some of the slip agent is partially embedded in the inner surface.

62. The endoscope assembly according to claim 61 wherein the slip agent comprises a granular slip agent.

63. The endoscope assembly according to claim 61 wherein the tubular portion is formed of an impermeable polymeric material and wherein the inner surface includes a textured portion having a plurality of surface features formed of the impermeable polymeric material, the tubular portion further having a smooth outer surface opposite from the inner surface.

64. The endoscope assembly according to claim 63 wherein the surface features comprise longitudinally disposed grooves.

65. The endoscope assembly according to claim 63 wherein the surface features comprise non-uniformly spaced surface features.

66. An endoscope assembly, comprising:
an endoscope including an elongated insertion tube; and
a sheath having an elongated, tubular portion at least partially encapsulating the insertion tube, the tubular portion being formed of an impermeable polymeric material and having an inner surface proximate the insertion tube and an outer surface opposite from the inner surface, at least a portion of the outer surface including a treating agent comprising a medication.

67. The endoscope assembly according to claim 66 wherein the treating agent includes a slip agent.

68. The endoscope assembly according to claim 67 wherein at least some of the slip agent is partially embedded in the outer surface.

69. The endoscope assembly according to claim 66 wherein the medication comprises an anti-inflammatory medication.

70. The endoscope assembly according to claim 66 wherein the medication comprises an anesthetic.

71. A sheath adapted for use with an endoscopic insertion tube, comprising:
an elongated, tubular portion formed of an impermeable polymeric material and having an inner surface substantially surrounding a volume adapted to receive and extend substantially about the insertion tube, and an outer surface opposite from the inner surface, at least a portion of the outer surface including a treating agent comprising a medication that includes an anesthetic.

72. The sheath according to claim 71 wherein the tubular portion comprises an elastic tubular portion.

73. The sheath according to claim 71 wherein the treating agent includes a slip agent.

74. The sheath according to claim 73 wherein at least some of the slip agent is partially embedded in the outer surface.

75. The sheath according to claim 73 wherein the slip agent comprises a granular slip agent.

76. The sheath according to claim 73 wherein the slip agent comprises a liquid slip agent.

77. The sheath according to claim 71 wherein the medication additionally comprises an anti-inflammatory medication.

78. A method of forming a sheath adapted to be engageable with an endoscopic insertion tube, comprising:
providing a sheet of impermeable polymeric sheath material;
forming the sheet into a tubular sheath sized and shaped to at least partially receive the endoscopic insertion tube; and
applying a treating agent including a medication to a surface of the sheet of sheath material that forms an outer surface of the tubular sheath and wherein the medication includes an anti-inflammatory.

79. The method according to claim 78 wherein applying a treating agent to a surface of the sheet of sheath material that forms an outer surface additionally comprises applying an anesthetic to a surface of the sheet of sheath material that forms an outer surface.

80. The method according to claim 78 wherein applying a treating agent to a surface of the sheet of sheath material that forms an outer surface comprises partially embedding a treating agent into a surface of the sheet of sheath material that forms an outer surface.

81. The method according to claim 78 wherein applying a treating agent to a surface of the sheet of sheath material comprises applying a treating agent to a surface of the sheet of sheath material simultaneously with forming the sheet into a tubular sheath.

82. A method of forming a sheath adapted to be engageable with an endoscopic insertion tube, comprising:

provining a sheet of impermeable polymeric sheath material;

forming the sheet into a tubular sheath sized and shaped to at least partially receive the endoscopic insertion tube; and applying a treating agent including a medication to a surface of the sheet of sheath material that forms an outer surface of the tubular sheath and wherein the medication includes an anesthetic.

83. The method according to claim 82 wherein applying a treating agent to a surface of the sheet of sheath material that forms an outer surface additionally comprises applying an anti-inflammatory to a surface of the sheet of sheath material that forms an outer surface.

84. The method according to claim 82 wherein applying a treating agent to a surface of the sheet of sheath material that forms an outer surface comprises partially embedding a treating agent into a surface of the sheet of sheath material that forms an outer surface.

85. The method according to claim 82 wherein applying a treating agent to a surface of the sheet of sheath material comprises applying a treating agent to a surface of the sheet of sheath material simultaneously with forming the sheet into a tubular sheath.

86. An endoscope assembly, comprising:

an endoscope including an elongated insertion tube; and a sheath having an elongated, tubular portion at least partially encapsulating the insertion tube, the tubular portion further having an inner surface proximate the insertion tube, at least a portion of the inner surface including a slip agent, wherein the tubular portion is formed of an impermeable polymeric material, and wherein the inner surface includes a textured portion having a plurality of surface features formed of the impermeable polymeric material, the tubular portion further having a smooth outer surface opposite from the inner surface.

87. The endoscope assembly according to claim 86 wherein at least some of the slip agent is partially embedded in the inner surface.

88. The endoscope assembly according to claim 86 wherein the slip agent comprises a granular slip agent.

89. The endoscope assembly according to claim 86 wherein the surface features comprise longitudinally disposed grooves.

90. The endoscope assembly according to claim 86 wherein the surface features comprise non-uniformly spaced surface features.

* * * * *

UNITED STATES PATENT AND TRADEMARK OFFICE
CERTIFICATE OF CORRECTION

PATENT NO.    : 6,530,881 B1                                            Page 1 of 1
DATED         : March 11, 2003
INVENTOR(S)   : Robert E. Ailinger et al.

It is certified that error appears in the above-identified patent and that said Letters Patent is hereby corrected as shown below:

Column 2,
Line 62, "sheath made form" should read -- sheath made from --

Column 3,
Line 15, "the insertions tube" should read -- the insertion tube --
Line 27, "with a relative thick" should read -- with a relatively thick --

Column 4,
Line 42, "according an embodiment" should read -- according to an embodiment --

Column 5,
Line 24, "device, for example an" should read -- device, for example, an --
Line 46, "and stretched wall" should read -- and a stretched wall --
Line 47, "diameter, and a" should read -- diameter, and --

Column 11,
Line 53, "sheet, or otherwise" should read -- sheet or otherwise --
Line 61, "calendaring or casting" should read -- calendering or casting --

Signed and Sealed this

Thirtieth Day of March, 2004

JON W. DUDAS
*Acting Director of the United States Patent and Trademark Office*